(12) United States Patent
Chao et al.

(10) Patent No.: US 8,535,926 B2
(45) Date of Patent: Sep. 17, 2013

(54) CELLULASES WITH HIGH ACTIVITIES

(75) Inventors: Yu-Chan Chao, Taipei (TW);
Chia-Jung Chang, Kaohsiung-Hsien (TW)

(73) Assignee: Academia Sinica, Taipei (TW)

(*) Notice: Subject to any disclaimer, the term of this patent is extended or adjusted under 35 U.S.C. 154(b) by 278 days.

(21) Appl. No.: 13/046,765

(22) Filed: Mar. 13, 2011

(65) Prior Publication Data

US 2012/0231507 A1  Sep. 13, 2012

(51) Int. Cl.
*C12P 19/00* (2006.01)
*C12N 9/42* (2006.01)

(52) U.S. Cl.
USPC .......... 435/209; 435/72; 435/320.1; 536/23.2

(58) Field of Classification Search
None
See application file for complete search history.

(56) References Cited

PUBLICATIONS

Lee, S.J., Lee, K.S., Kim, S.R., Gui, Z.Z., Kim, Y.S., Yoo, H.J. et al. (2005) "A novel cellulase gene from the mulberry longicorn beetle, Apriona germari: gene structure, expression, and enzymatic activity" Comp Biochem Physiol B 140: 551-560.

Sugimura, M. Watanabe, H., Lo, N. and Saito, H. (2003) "Purification, characterization,cDNA cloning and nucleotide sequencing of a cellulase from the yellow-spottedlongicorn beetle, Psacothea hilaris" Eur J Biochem 270:3455-3460.

*Primary Examiner* — Lisa J Hobbs
(74) *Attorney, Agent, or Firm* — Hsiu-Ming Saunders; Intellectual Property Connections, Inc.

(57) ABSTRACT

Two novel cellulases and nucleotide sequences encoding the same are disclosed. Also disclosed are compositions and methods for using the same for hydrolyzing cellulosic waste materials.

20 Claims, 11 Drawing Sheets

SEQ ID NO: 1 (AmCel-45A cDNA)
SEQ ID NO: 2 (AmCel-45A protein)

```
        Met Lys Leu Leu Leu Leu Ile Ala Ala Val Phe Tyr Thr Phe His Gly Ser
  1     ATG AAG CTG TTG TTA CTA ATT GCT GCT GTG TTT TAC ACA TTC CAT GGA TCG
        Phe Ser Lys Asp Tyr Asn Val Val Pro Ile Val Gly Gly Ile Ser Gly Thr
  51    TTC TCC AAA GAC TAC AAT GTC GTG CCA ATA GTG GGC GGC ATA AGT GGA ACC
        Gly Val Thr Thr Arg Tyr Trp Asp Cys Cys Lys Pro Ser Cys Gly Trp Ala
  101   GGA GTC ACA ACC CGT TAC TGG GAC TGT TGT AAA CCG TCA TGT GGT TGG GCT
        Glu Asn Leu Lys Val Glu Thr Asp Thr Pro Val Ala Thr Cys Ser Ala Asp
  151   GAA AAT TTG AAA GTC GAA ACT GAC ACC CCT GTA GCG ACT TGT TCA GCT GAC
        Gly Ser Thr Val Val Asn Ala Ser Val Gln Ser Ala Cys Ile Gly Gly Asp
  201   GGA TCA ACT GTA GTA AAC GCC AGC GTC CAA TCA GCT TGT ATA GGA GGC GAT
        Ala Tyr Met Cys Ser Asn Gln Gln Pro Lys Ala Val Asn Glu Thr Phe Ala
  251   GCT TAC ATG TGC AGT AAT CAA CAA CCC AAA GCG GTC AAT GAA ACG TTT GCT
        Leu Gly Phe Val Ala Ala Ser Phe Thr Gly Gly Ala Asp Thr Asn Tyr Cys
  301   CTT GGA TTT GTG GCT GCT TCC TTC ACC GGA GGT GCC GAT ACC AAC TAT TGT
        Cys Ala Cys Val Arg Leu Thr Phe Gln Ser Pro Ile Gln Gly Lys Gln Met
  351   TGT GCT TGT GTG CGA CTT ACC TTC CAG TCT CCT ATT CAA GGC AAA CAG ATG
        Val Val Gln Val Thr Asn Thr Gly Gly Asp Leu Gly Ser Asn His Phe Asp
  401   GTT GTA CAA GTA ACC AAT ACT GGT GGT GAT TTG GGT TCC AAT CAT TTT GAC
        Ile Ala Leu Pro Gly Gly Gly Val Gly Ile Phe Thr Glu Gly Cys Ser Ser
  451   ATC GCC CTT CCC GGT GGT GGT GTG GGA ATA TTC ACT GAA GGT TGT TCT TCG
        Gln Trp Gly Cys Pro Ser Asn Gly Trp Gly Asp Gln Tyr Gly Gly Val Ala
  501   CAA TGG GGA TGT CCT AGC AAT GGC TGG GGT GAC CAG TAT GGC GGT GTT GCA
        Ser Glu Ser Asp Cys Ser Thr Leu Pro Ala Val Leu Gln Asp Gly Cys Lys
  551   TCG GAA AGT GAC TGT TCT ACA CTT CCA GCA GTC CTC CAA GAT GGA TGT AAA
        Phe Arg Phe Gln Phe Leu Gln Gly Ala Ser Asn Pro Gly Val Thr Phe Glu
  601   TTC CGT TTT CAG TTC CTG CAA GGC GCG TCT AAC CCT GGT GTT ACC TTT GAA
        Gln Val Glu Cys Pro Ser Glu Leu Thr Ser Ile Thr Gly Cys Asn Tyr Ser
  651   CAA GTC GAG TGT CCA TCC GAG TTG ACA TCT ATT ACT GGC TGT AAC TAT TCC
        ***
  701   TAA
```

FIG. 1

SEQ ID NO: 3 (AmCel-5B cDNA)
SEQ ID NO: 4 (AmCel-5B protein)

```
           Met Asn Lys Ser Ile Leu Ser Ile Cys Leu Val Val Leu Ala Leu Tyr Ile
  1        ATG AAC AAG TCA ATT TTG TCG ATT TGT CTG GTC GTG CTG GCC TTG TAT ATC
           Asp Ser Ser Ile Ser Lys Asp Ala Gly Gln Glu Thr Val Ser Lys His Gly
 51        GAT TCC TCG ATA TCT AAG GAT GCC GGC CAA GAA ACA GTT TCC AAG CAC GGT
           Lys Leu Ser Val Lys Gly Ala Asn Ile Val Asn Gln Asn Gly Glu Ile Val
101        AAA CTG TCC GTG AAG GGT GCC AAC ATA GTG AAC CAG AAT GGC GAG ATA GTC
           Gln Leu Lys Gly Met Cys Leu Tyr Trp Ser Ile Trp Lys Pro Gln Tyr Trp
151        CAG TTG AAA GGC ATG TGT TTG TAC TGG AGC ATA TGG AAG CCA CAG TAC TGG
           Asn Glu Glu Thr Val Gln Gly Ile His Asp Ser Cys His Ser Asn Val Ile
201        AAC GAA GAA ACA GTC CAA GGA ATT CAC GAC TCG TGT CAC TCC AAC GTT ATC
           Arg Ala Ser Met Gly Val Glu Thr Asn Asp Gly Gly Tyr Leu Thr Asp Pro
251        CGA GCT TCC ATG GGC GTC GAG ACA AAC GAT GGC GGT TAC TTA ACT GAC CCA
           Asp Gly Gln Met Lys Leu Val Glu Thr Val Ile Glu Ala Ala Ile Lys His
301        GAC GGT CAG ATG AAG CTA GTG GAA ACC GTC ATC GAG GCA GCA ATT AAA CAT
           Asp Leu Tyr Ile Ile Val Asp Trp His Glu Glu Lys Ala Gly Thr His Gln
351        GAC CTC TAC ATC ATC GTG GAC TGG CAC GAA GAA AAG GCA GGC ACT CAC CAA
           Thr Gln Ala Val Asp Phe Phe Asp Lys Ile Ser Lys Lys Tyr Gly Ser Tyr
401        ACA CAA GCT GTA GAC TTC TTT GAC AAA ATC TCT AAG AAA TAT GGA AGC TAC
           Pro Asn Leu Met Tyr Glu Thr Phe Asn Glu Pro Thr Thr Gln Ser Trp Ser
451        CCA AAT CTC ATG TAC GAA ACC TTC AAC GAA CCA ACT ACC CAG TCC TGG TCC
           Ser Val Leu Lys Pro Tyr His Glu Ala Val Ile Lys Ala Ile Arg Ala Asn
501        AGC GTG CTT AAA CCG TAT CAT GAA GCC GTT ATC AAA GCC ATC CGT GCC AAT
           Asp Pro Asp Asn Ile Ile Ile Cys Gly Thr Gly Gln Trp Ser Gln Arg Val
551        GAC CCA GAC AAC ATC ATC ATT TGC GGT ACT GGC CAA TGG TCA CAG AGA GTC
           Asp Glu Ala Ala Asp Asp Pro Ile Thr Ser Tyr Ser Asn Ile Met Tyr Thr
601        GAC GAA GCC GCC GAT GAT CCT ATC ACG AGC TAC AGC AAT ATC ATG TAC ACT
           Leu His Phe Tyr Ala Gly Thr His Lys Gln Trp Leu Arg Asp Leu Thr Gln
651        TTG CAC TTC TAC GCT GGC ACC CAT AAG CAA TGG CTC CGT GAC CTC ACT CAA
           Gly Ala Ile Asp Lys Gly Leu Pro Ile Phe Val Thr Glu Tyr Gly Thr Asp
701        GGC GCT ATC GAC AAA GGT CTT CCC ATC TTC GTT ACA GAA TAT GGC ACT GAT
           Asn Val Asp Val Val Asn Trp Val Asp Pro Glu Glu Ser Gln Leu Trp Trp
751        AAT GTA GAT GTG GTC AAT TGG GTG GAT CCC GAA GAA TCC CAG CTT TGG TGG
           Asp Phe Cys Asp Lys Asn Asn Leu Ser Tyr Thr Asn Trp Ala Ile Cys Asp
801        GAC TTC TGT GAT AAA AAT AAC TTG TCC TAT ACT AAC TGG GCC ATA TGC GAC
           Val Ala Glu Ala Ser Ala Ala Leu Ile Ala Asp Thr Pro Pro Asn Lys Val
851        GTG GCC GAG GCA TCT GCT GCT TTG ATA GCA GAC ACC CCC CCC AAT AAA GTA
           Cys Gln Gln Asp Tyr Leu Thr Glu Ser Gly Leu Leu Val Val Ala Gln Asn
901        TGC CAA CAA GAT TAC CTG ACG GAA TCC GGC TTG CTC GTT GTA GCC CAG AAT
           Lys ***
           AAA TGA
```

FIG. 2

CELLULASES WITH HIGH ACTIVITIES

FIELD OF THE INVENTION

The present invention relates generally to cellulases, and more specifically to novel cellulases with high activities.

BACKGROUND OF THE INVENTION

Cellulases, cellulose (highly-polymerized β-1,4-glucan)-degrading enzymes, generally include cellobiohydrolase (targeting mainly crystalline cellulose) and endo-1,4-β-endoglucanase (targeting mainly amorphous cellulose). For the generation of cellulosic bio-energy, it is important to identify highly active cellulases to improve the efficiency of cellulose decomposition.

SUMMARY OF THE INVENTION

In one aspect, the invention relates to a composition comprising: a) a first cellulase, comprising an amino acid sequence having at least 95%, 90%, 85%, 80%, 75% or 70% identity to SEQ ID NO: 2; and b) a second cellulase, comprising an amino acid sequence having at least 95%, 90%, 85%, 80%, 75%, 70% or 65% identity to SEQ ID NO: 4.

In another aspect, the invention relates to a method of hydrolyzing cellulosic material. The method comprises exposing the cellulosic material to an effective amount of a composition as aforementioned.

In another aspect, the invention relates to an isolated cellulase comprising an amino acid sequence having at least 95%, 90%, 85% or 80% identity to an amino acid sequence selected from the group consisting of SEQ ID NOs: 2 and 4.

Further in another aspect, the invention relates to an isolated nucleic acid sequence encoding the cellulase as aforementioned.

Further in another aspect, the invention relates to a recombinant vector for expression of a cellulase, the recombinant vector comprising: (a) at least one regulatory element; and (b) an isolated nucleic acid sequence encoding the cellulase as aforementioned, linked in translation frame to the at least one regulatory element.

Yet in another aspect, the invention relates to an isolated cellulase generated from a recombinant vector as aforementioned.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 1 shows the nucleotide sequence of AmCel-45A cDNA (SEQ ID NO: 1) and the encoded amino acid sequence (SEQ ID NO: 2) from Taiwan white spotted longicorn beetle, *Anoplophora malasiaca*.

FIG. 2 shows the nucleotide sequence of AmCel-5B cDNA (SEQ ID NO: 3) and the encoded amino acid sequence (SEQ ID NO: 4) from Taiwan white spotted longicorn beetle, *Anoplophora malasiaca*.

In FIG. 9A, the concentrations of the chemicals were 2 mM (gray) and 10 mM (dark gray), respectively. Each enzyme activity was normalized and expressed as a percentage of the control measured in 1% CMC, 50 mM citrate buffer, pH 4.0 at 50° C. for 1 hr. FIG. 9B shows the effects of different metal ions on AmCel-45A activity in the presence of 10 mM DTT. Concentrations of ions were 2 mM (gray) and 10 mM (dark gray). The dashed line represents the control.

In FIG. 10A, the concentrations of the chemicals were 2 mM (gray) and 10 mM (dark gray), respectively. Each enzyme activity was normalized and expressed as a percentage of the control measured in 1% CMC, 50 mM citrate buffer, pH 4.0 at 50° C. for 1 hr. FIG. 10B shows the effects of different metal ions on AmCel-5B activity in the presence of 10 mM DTT. Concentrations of ions were 2 mM (gray) and 10 mM (dark gray).

DETAILED DESCRIPTION OF THE INVENTION

Definitions

Figure 3:
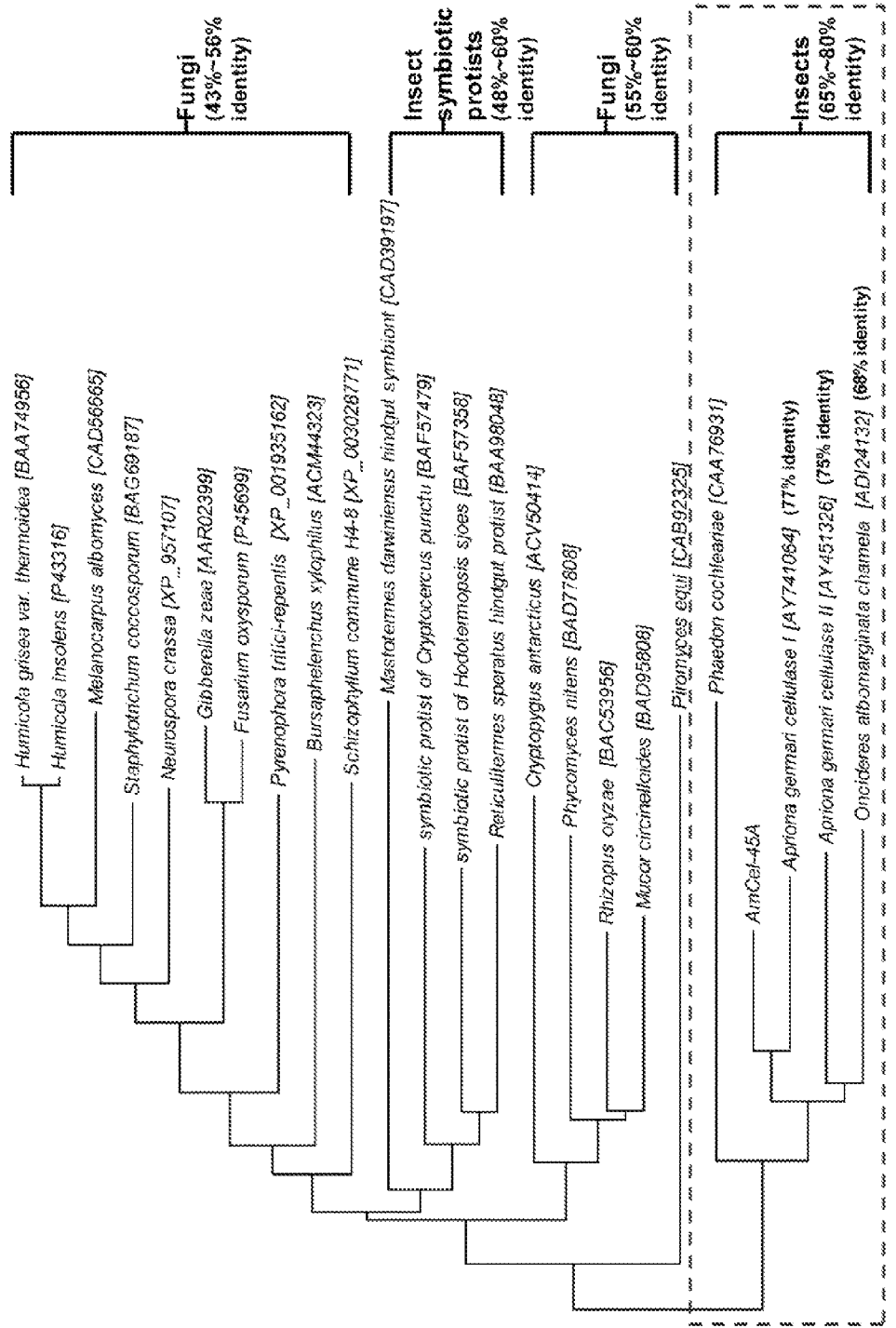
FIG. 3 is a phylogenetic tree (or evolutionary tree) based on the amino acid sequences of cellulases from the glycoside hydrolase family (GHF) 45 showing that the AmCel-45A from *Anoplophora malasiaca* was similar to the endo-β-1,4-glucanase from *Apriona germari* (Longicorn), *Oncideres albomarginata chamela* (beetle) and *Phaedon cochleariae* (beetle) (about 65-80% identity in the amino acid sequences).

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "cellulase" refers to a class of enzymes that catalyze cellulolysis (i.e. the hydrolysis of cellulose). There are five general types of cellulases based on the type of reaction catalyzed. Endo-cellulase breaks internal bonds to disrupt the crystalline structure of cellulose and expose individual cellulose polysaccharide chains. Exo-cellulase cleaves 2-4 units from the ends of the exposed chains produced by endocellulase, resulting in the tetrasaccharides or disaccharide such as cellobiose. There are two main types of exo-cellulases (or cellobiohydrolases, abbreviate CBH)-one type working processively from the reducing end, and one type working processively from the non-reducing end of cellulose. Cellobiase or beta-glucosidase hydrolyses the exo-cellulase product into individual monosaccharides. Oxidative cellulases that depolymerize cellulose by radical reactions, as for instance cellobiose dehydrogenase (acceptor). Cellulose phosphorylases that depolymerize cellulose using phosphates instead of water. The three types of reaction catalyzed by cellulases are: (1) Breakage of the non-covalent interactions present in the crystalline structure of cellulose (endo-cellulase); (2) Hydrolysis of the individual cellulose fibers to break it into smaller sugars (exo-cellulase); and (3) Hydrolysis of disaccharides and tetrasaccharides into glucose (beta-glucosidase).

The term "cellulose" is an organic compound with the formula $(C_6H_{10}O_5)_n$, a polysaccharide consisting of a linear chain of several hundred to over ten thousand β(1→4) linked D-glucose units. Cellulose is the structural component of the primary cell wall of green plants. Converting cellulose from energy crops into biofuels such as cellulosic ethanol is under investigation as an alternative fuel source.

The terms "percent identity" is used to quantify the identity between the biomolecule sequences. For two naturally occurring sequences, percent identity is a factual measurement. As used herein, "percentage sequence identity" is equal to (the number of identical residues divided by the average length of two sequences in comparison) times 100%. The degree to which two sequences in a query set are different is related to the evolutionary distance from each another. A sequence identity may be acquired by using NCBI blastX online.

The invention relates to the discovery of two cellulases from Taiwanese white spotted longicorn beetle *Anoplophora malasiaca*. Both cellulases have unique nucleotide sequences that are significantly different from all genes disclosed in the public domain (with a similarity of less than 60% to all the published genes on discontinuous megablast). Also, the enzyme AmCel-5B is so far the only cellulase identified from insects with exo-cellulase activity.

Briefly, two novel insect endogenous cellulase genes of distinct glycoside hydrolase family (GHFs) were isolated and cloned from Taiwan local white spotted longicorn beetle, *Anoplophora malasiaca*. Through baculovirus expression in silkworms and purification, AmCel-45A was produced and the protein had strongest endo-glucanase activity. AmCel-5B had higher crystalline cellulose hydrolysis activity than AmCel-45A. AmCel-5B is a unique cellulase in that it contains endo-glucanase, exo-glucanase and some hemi-cellulase activity. These enzymes exhibited a strong activity when they were combined with commonly used commercial cellulases, the combination exhibiting 8× higher activity than CELLUCLAST® 1.5 L used alone in row lignocellulose hydrolysis. The discovery is important in cutting down the cost for using the cellulases for bioenergy production. Therefore, the invention is highly commercially valuable in generation of bioenergy from rice straw, an abundant material and previously regarded as a waste and for clean energy in the future.

In one aspect, the invention relates to a composition comprising: a) a first cellulase, comprising an amino acid sequence having at least 95%, 90%, 85%, 80%, 75% or 70% identity to SEQ ID NO: 2; and b) a second cellulase, comprising an amino acid sequence having at least 95%, 90%, 85%, 80%, 75%, 70% or 65% identity to SEQ ID NO: 4.

In one embodiment of the invention, the composition comprises: a) a first cellulase, comprising an amino acid sequence having at least 95%, 90%, 85% or 80% identity to SEQ ID NO: 2; and b) a second cellulase, comprising an amino acid sequence having at least 95%, 90%, 85%, 80%, 75% 70%, or 65% identity to SEQ ID NO: 4.

In another embodiment of the invention, the composition as aforementioned may further comprise at least a metal ion or an antioxidant agent.

In another embodiment of the invention, the composition may further comprise at least one additional commercial cellulase.

In another aspect, the invention relates to a method of hydrolyzing cellulosic material. The method comprises exposing the cellulosic material to an effective amount of a composition as aforementioned.

Further in another aspect, the invention relates to an isolated cellulase comprising an amino acid sequence having at least 95%, 90%, 85% or 80% identity to an amino acid sequence selected from the group consisting of SEQ ID NOs: 2 and 4.

In one embodiment of the invention, the isolated cellulase comprises an amino acid sequence having at least 95%, 90%, 85% or 80% identity to SEQ ID NO: 2.

In another embodiment of the invention, the isolated cellulase comprises an amino acid sequence having at least 95%, 90%, 85%, 80%, 75% 70%, or 65% identity to SEQ ID NO: 4.

In another embodiment of the invention, the isolated cellulase comprises the amino acid sequence selected from the group consisting of SEQ ID NOs: 2 and 4.

Further in another aspect, the invention relates to an isolated nucleic acid sequence encoding the cellulase as aforementioned.

In one embodiment of the invention, the isolated nucleic acid sequence encoding a cellulase as aforementioned comprises a nucleotide sequence chosen from SEQ ID NOs: 1 and 3.

Further in another aspect, the invention relates to a recombinant vector for expression of a cellulase, the recombinant vector comprising: (a) at least one regulatory element; and (b) an isolated nucleic acid sequence encoding the cellulase as aforementioned, linked in translation frame to the at least one regulatory element.

In one embodiment of the invention, the recombinant vector is a baculovirus expression vector.

In another embodiment of the invention, the recombinant vector for expression of a cellulase comprises: (a) at least one regulatory element; and (b) an isolated nucleic acid sequence as aforementioned, linked in translation frame to the at least one regulatory element.

Yet in another aspect, the invention relates to an isolated cellulase generated from a recombinant vector as aforementioned.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Methods and Materials

Construction of Insect cDNA Library and Screening Candidate Genes

The larvae of white spotted longicorn beetle, *A. malasiaca*, were ground on dry ice and pure mRNA isolated from the whole sample. A cDNA library was established from the mRNA by using a CREATOR™ SMART™ cDNA Library Construction Kit (Clontech). Degenerate primers were designed based on conserved catalytic domains of GHF 45 and GHF5 eukaryotic cellulases. The total cDNAs of *A. malasiaca* were used as templates. Degenerate primers and DIG-dUTP were used for PCR amplification to generate hybridization probes labeled with DIG. These probes were used for detection of target cellulase genes. The DIG positive cDNA fragments-containing colonies were further extracted, sequenced and analyzed.

Rapid Amplification of cDNAs (5' RACE) of Insect Cellulase Genes

SMART™ RACE cDNA Amplification Kit (Clontech) was used to amplify 5' ends of target cDNAs. The mRNA of *A. malasiaca* was the template for the first strand cDNA synthesis. Gene-specific primer was designed base on the sequence of the target cDNA to amplify 5' fragments. Then double-stranded full-length cDNA with additional sequences encoding C-terminus polyhistidine tag was cloned into the BmNPV baculovirus transfer vector pBPxhE with SacI and NotI digestion. The transfer vector pBPxhE contains a baculovirus strong late promoter (p pol; polyhedron promoter) to drive foreign protein expression and a general promoter (hsp; heat shock promoter) to drive green fluorescence protein (GFP) expression used as a recombinant marker.

Expression of Recombinant AmCel-45A and AmCel-5B in Silkworm Larvae and Purification The recombinant viruses were selected based on GFP expression. The isolated BmNPV recombinant virus was titrated by end-point dilution and high-titer stocks ($10^8$ p.f.u./ml) were used for infecting cells and larvae. *Bombyx. mori* larvae from the first day of fifth instar were injected with the recombinant virus into the haemocoel at the third abdominal piracies. The larvae were reared on mulberry leaves for the entire infection period (3-4 days). For affinity chromatography purification of recombinant AmCel-45A and AmCel-5B, the body fluid of infected silkworm was collected with addition of N-phenylthiourea. The solution was centrifuged at 13,000×g for 20 min at 4° C. to remove cell debris. The supernatant was filtered to remove lipids. The filtration was diluted with native binding buffer (50 mM $NaH_2PO_4$, 300 mM NaCl, pH 7.5) and applied to HisPur Cobalt resin (Pierce) for overnight incubation. The AmCel-45A was eluted with elution buffer plus 250 mM imidazole, and eluted AmCel-5B was detectable in 100 mM imidazole fraction. These collected fractions were dialyzed and concentrated by the concentrator SPIN-X®20-10k (CORNING®). The protein samples were mixed with protein sample buffer, boiled and subjected to 12% SDS-PAGE. After electrophoresis, gels were fixed and stained with 0.1% Coomassie Brilliant Blue R-250. For Western blot analysis, proteins were blotted and detected by the $His_{(6)}$ monoclonal antibody (1:2500 v/v, Serotech) for overnight at 4° C.

Biochemical Characterization of AmCel-45A and AmCel-5B

Optimal temperature and thermo-stability. The AmCel-45A and Amcel-5B were incubated 1% (w/v) carboxymethyl cellulose (CMC; SIGMA®) in 50 mM citrate buffer (pH 5.0) at various temperatures 16° C., 26° C., 37° C., 50° C., 60° C. and 70° C. Thermo-stability was performed by pre-incubating at 16° C., 26° C., 37° C., 50° C., 60° C. and 70° C. for 12 hr. The residual activity was assayed with 1% CMC in 50 mM citrate buffer, pH 4.0, at 50° C. The amount of reducing sugars produced by these reactions was measured by the dinitrosalicylic acid (DNS) reagent method.

Optimal pH and acid and alkali tolerance. Endoglucanases were assayed with 1% (w/v) carboxymethyl cellulose in 50 mM buffer of different pH (pH 2.0-pH 10.0) at 50° C. For the pH tolerance, the purified enzymes were treated with 50 mM buffer of pH 2.0-pH 10.0 for 12 hr, and then the residual activity were measured with 1% CMC in 50 mM acetate buffer (pH 5.0) at 50° C. by the DNS method.

Effect of chemicals and metal ions. Several chemicals such as EDTA, $CaCl_2$, $CoCl_2$, $CuSO_4$, $MgCl_2$, $MnCl_2$, $ZnCl_2$, $NaN_3$, DTT, 2-mercaptoethanol and SDS at concentrations of 2 mM and 10 mM were separately mixed with 1% CMC assay buffer (50 mM citrate buffer, pH 4.0) at 50° C. for 1 hr and then the total reducing sugars were measured.

Substrate specificity. The AmCel-45A and AmCel-5B were analyzed with 1.0% different cellulose substrates, CMC, Avicel (SIGMA®), barley β-glucan (SIGMA®), Xylan-birchwood (SIGMA®), Xylan-oat spelts (Fluka), filter paper (Whatman No. 1) and pretreated rice straw fiber (acid-steam explored rice straw from AS-BCST) at the optimal conditions (pH temperature and additive chemicals).

Synergistic Combination of Insect Cellualses and Commercial Enzymes

The synergistic activity assay with commercial cellulase cocktail (CELLUCLAST® 1.5 L; Novozyme) was carried out by mixing a total of 100 µg of the combination of AmCel-45A, AmCel-5B and CELLUCLAST® 1.5 L with 1% of pretreated rice straw fibers in an optimal condition for 24 h. The residual cellulose was discarded by centrifugation at 13,000×g for 20 min and the concentration of the total reducing sugar was analyzed by the DNS method.

Results

Figure 4:
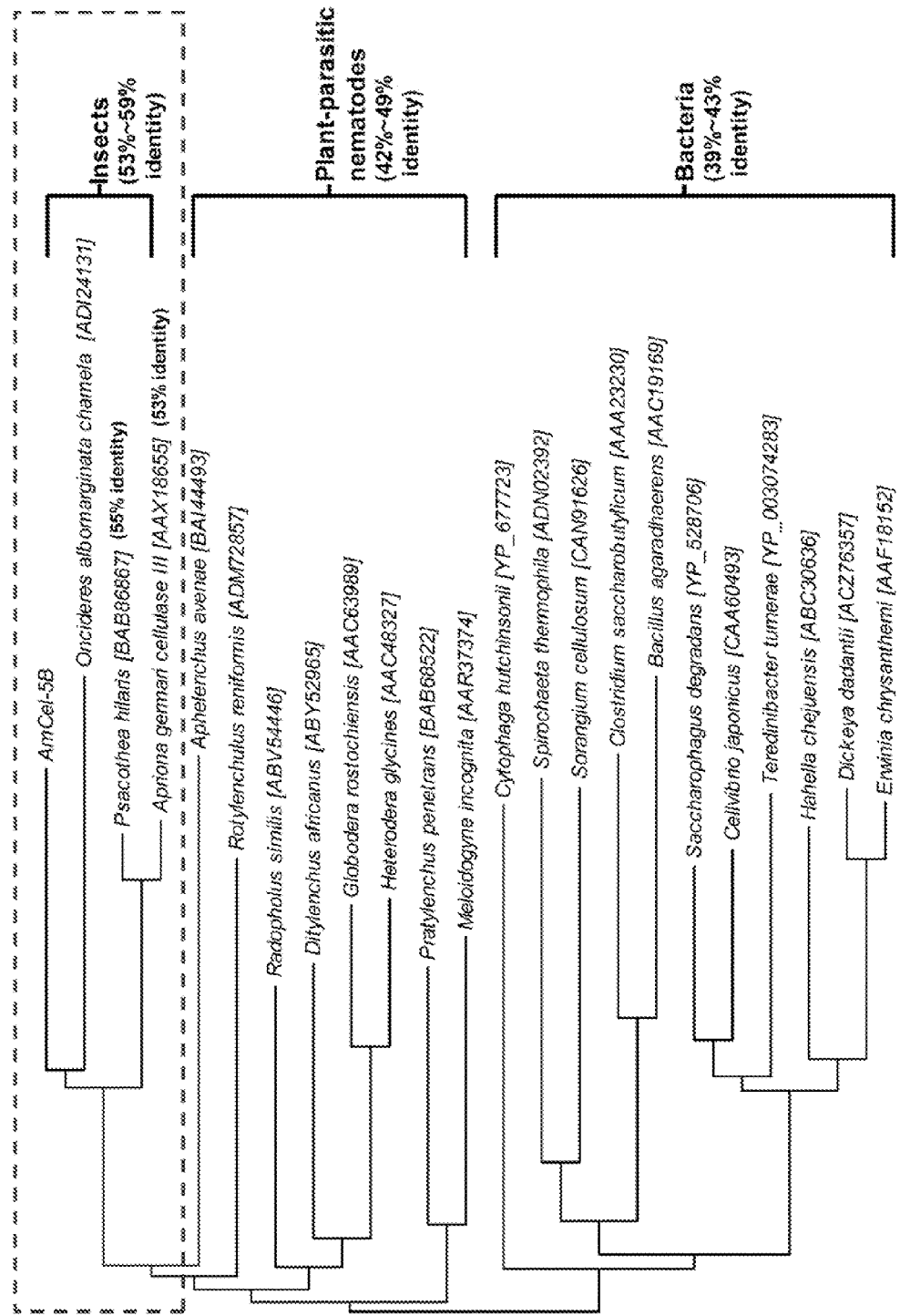
FIG. 4 is a phylogenetic tree based on the amino acid sequences of cellulases of glycoside hydrolase family (GHF) 5 showing that AmCel-5B from *Anoplophora malasiaca* was similar to the endo-β-1,4-glucanase of *Apriona germari* (Longicorn), *Oncideres albomarginata chamela* (beetle) and *Pracothea hilaris* (Longicorn) (about 53-59% identity in the amino acid sequences).

Two insect cellulase genes, AmCel-45A and AmCel-5B were found and cloned from the cDNA library of the Taiwan white spotted longicorn beetle *Anoplophora malasiaca*. The AmCel-45A cDNA had a size of 717 bps (including a signal sequence and a stop codon) and the AmCel-5B cDNA has a size of 978 bps (FIGS. 1 and 2). A search of nucleotide sequences in the NCBI megablast database indicated that AmCel-45A was closest to endo-1,4-β-endoglucanase of *Apriona germari* with 65% identity, and AmCel-5B closest to endo-1,4-β-endoglucanase of *Psacothea hilaris* with 53% identity. Based on the comparison of the translated amino acid sequences for the two new cellulases on NCBI protein blast, the AmCel-45A was closest to the insect endogenous endo-1,4-β-endoglucanase of *Apriona germari* (with 77% identity) and *Phaedon cochleariae* (with 68% identity) (FIG. 3); the AmCel-5B was closest to the insect endogenous cellulase of *Apriona germari* (with 53% identity) and *Psacothea hilaris* (with 55% identity) (FIG. 4). Based on the phylogenetic analyses, the two genes are insect endogenous cellulase genes instead of symbiotic genes and the insect cellulases formed a sub-group that could distinguish from other fungal or bacterial groups.

Figure 5:
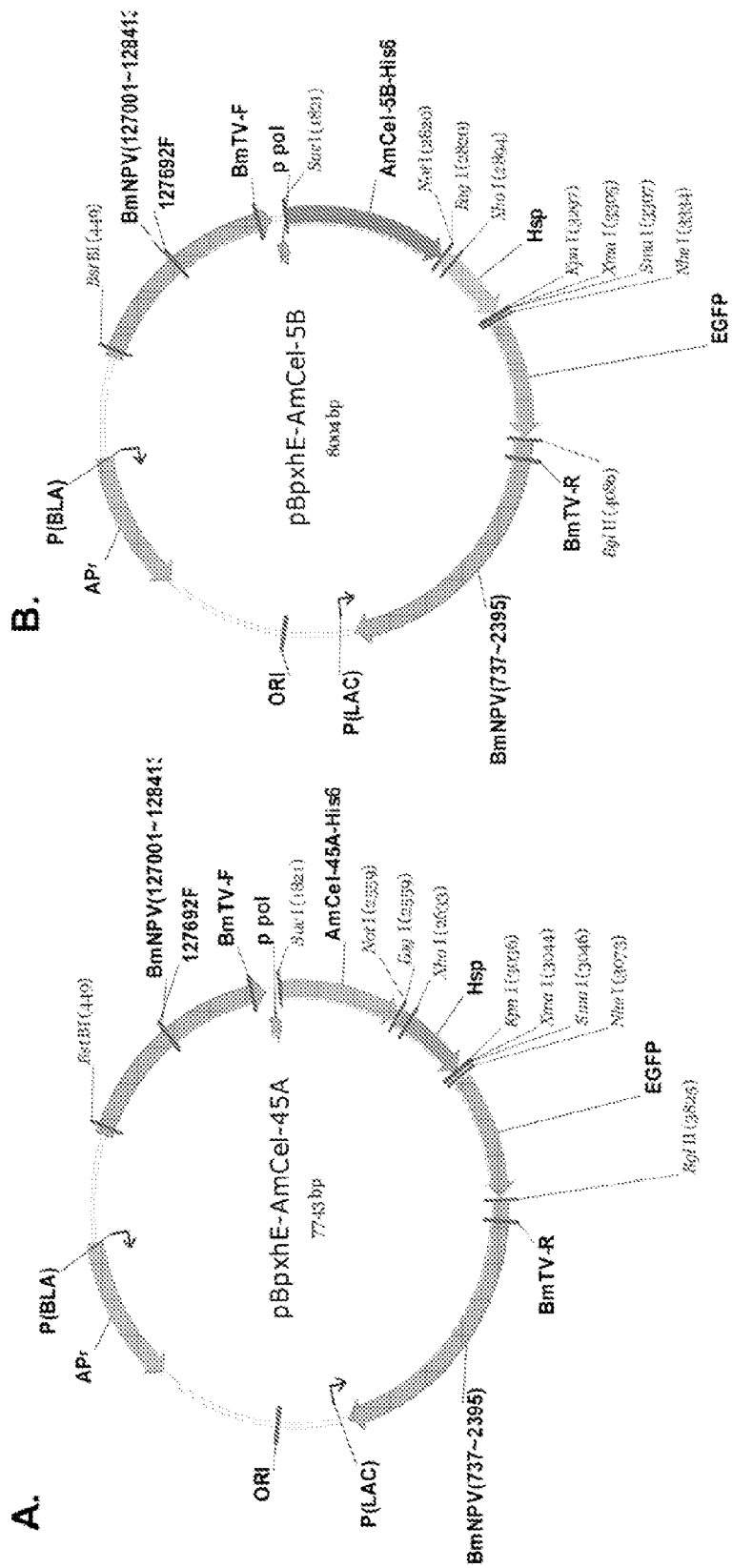
FIGS. 5A-5B are vector maps showing reconstructed pBpxhE plasmids comprising AmCel-45A (FIG. 5A) and AmCel-5B cDNA (FIG. 5B) for further application to a baculovirus expression system. The transfer vector pBPxhE contains baculovirus strong late promoter (p pol; polyhedron promoter) to drive foreign protein expression and general promoter (hsp; heat shock promoter) to drive green fluorescence protein (GFP) expression used as recombinant marker.
Figure 6:
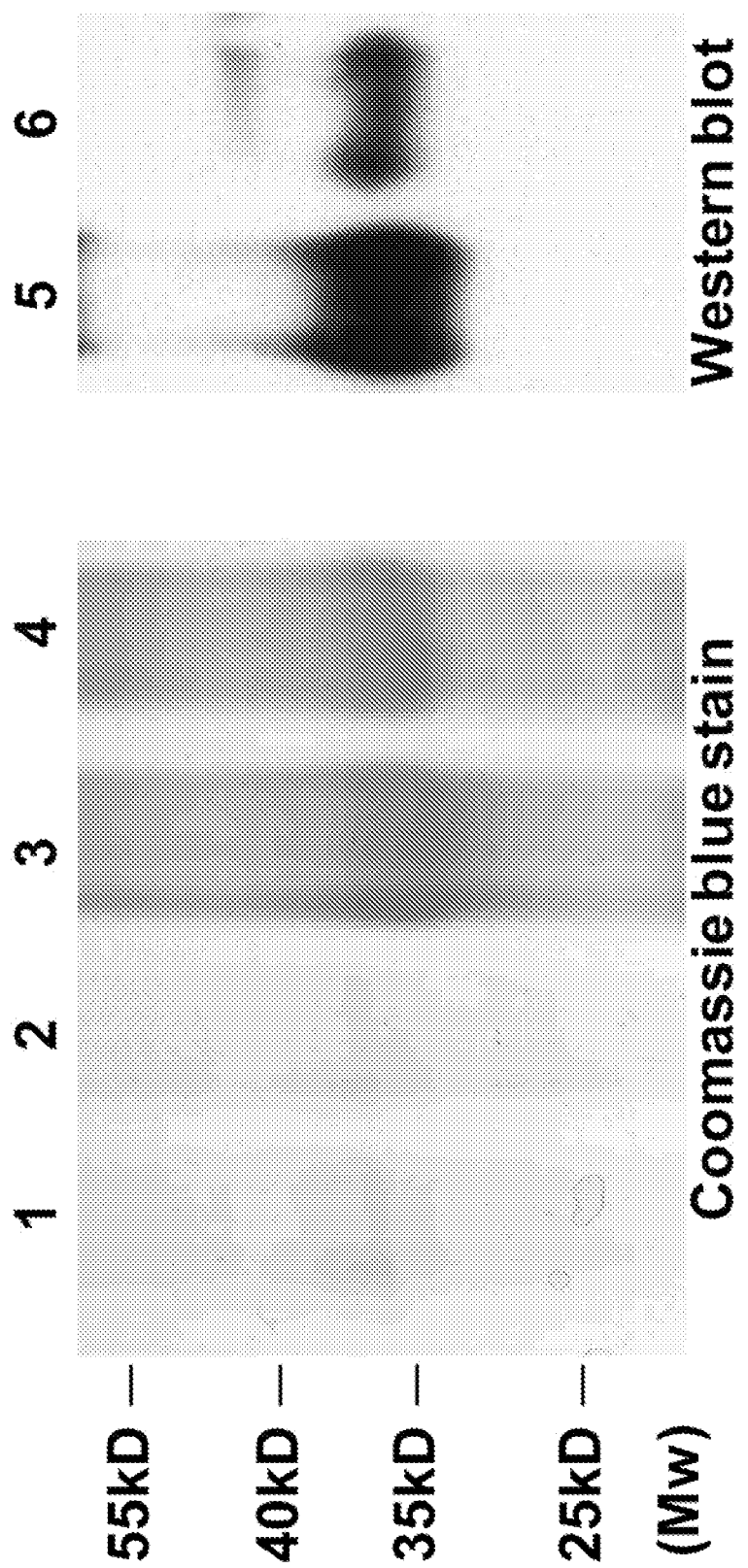
FIG. 6 shows the results of SDS-PAGE and Western blot analysis of purified recombinant AmCel-45A and AmCel-5B expressed in the baculovirus-infected silkworm body fluid. Lanes 1 and 3: purified AmCel-45A and concentrated protein. Lanes 2 and 4: purified AmCel-5B and concentrated protein. Lane 5: AmCel-45A anti-His$_{(6)}$ signal; Lane 6: AmCel-5B anti-His$_{(6)}$ signal.
Figure 7A:
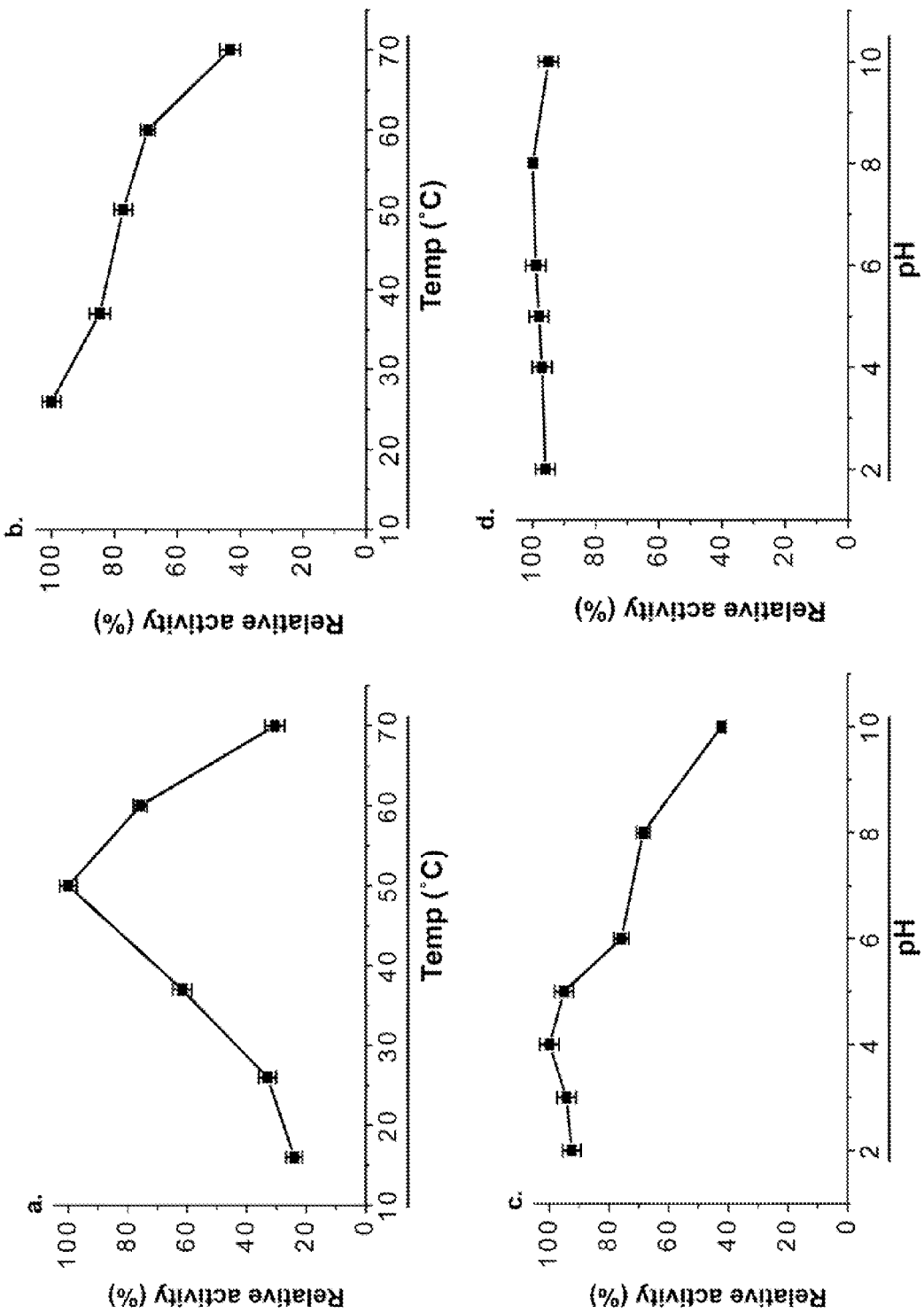
FIG. 7A shows the effects of pH and temperature on the activity and stability of AmCel-45A. a, optimal temperature. b, thermo-stability. c, optimal pH. d, pH tolerance.
Figure 7B:
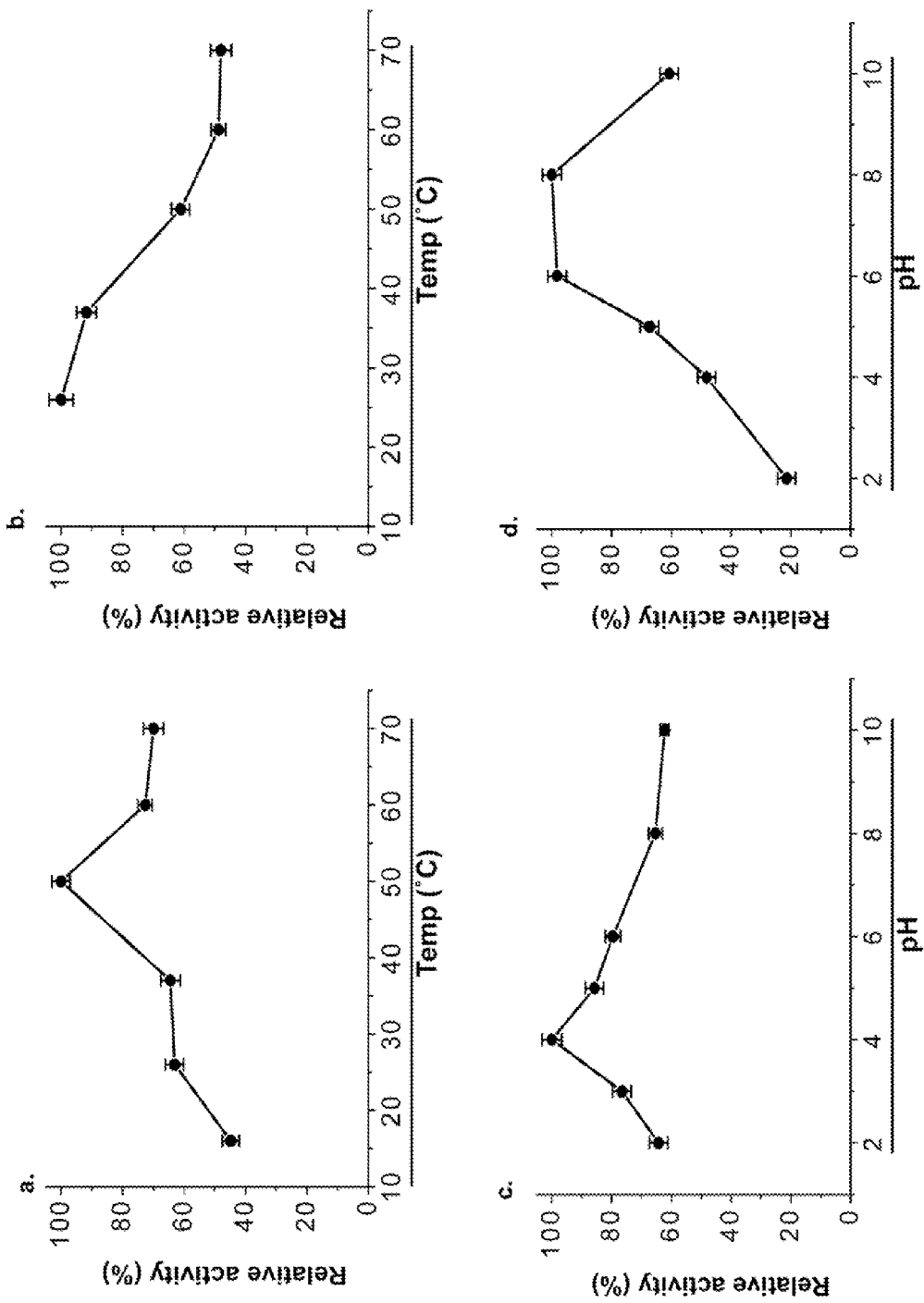
FIG. 7B shows the effects of pH and temperature on the activity and stability of AmCel-5B. a, optimal temperature. b, thermo-stability. c. optimal pH. d, pH tolerance.
Figure 8:
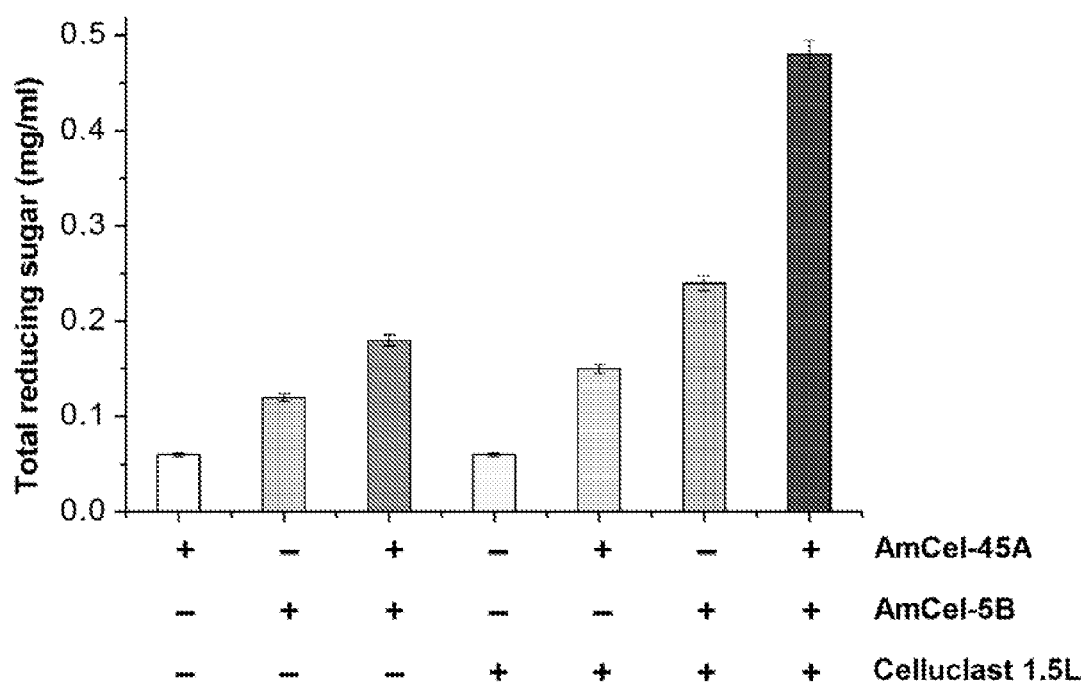
FIG. 8 shows the synergistic effect of insect cellulases and CELLUCLAST® 1.5 L in enzymatic hydrolysis of pre-treated rice straw. All experiments were performed on 1% pre-treated rice straw fibers (i.e., acid steam-explored rice straw), total 100 µg of cellulases (insect or/and commercial) at pH4.0, 50° C. for 24 h.
Figure 9:
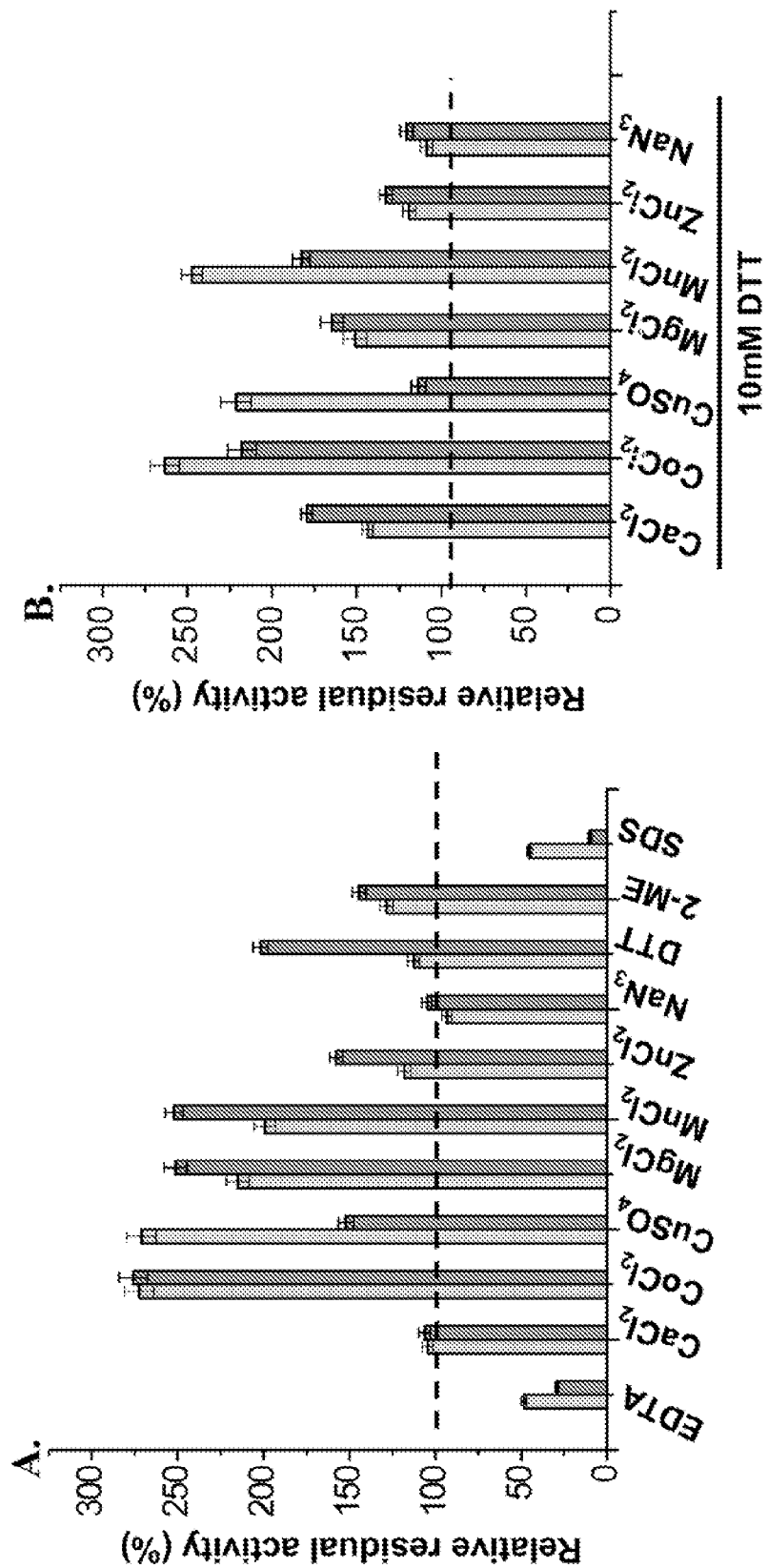
FIG. 9 shows the effects of metal ions and chemicals on AmCel-45A activity.
Figure 10:
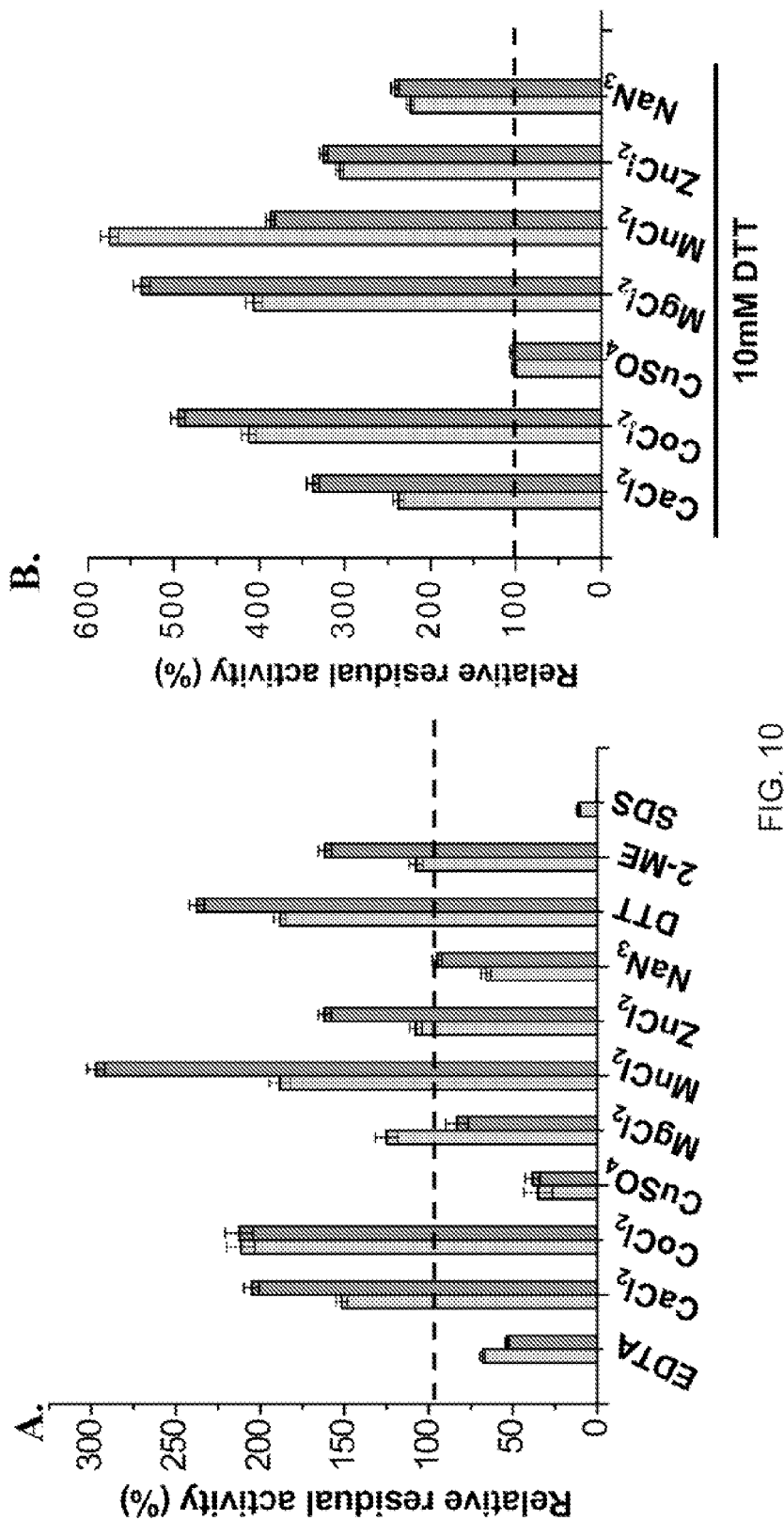
FIG. 10 shows the effects of metal ions and chemicals on AmCel-5B activity.

The AmCel-45A and AmCel-5B cDNA were further cloned into a pBpxhE transfer vector (FIG. 5) and transfected to select and produce recombinant BmNPV. By infection of silkworm larvae, the proteins of AmCel-45A and AmCel-5B were respectively expressed and further purified. The recombinant AmCel-45A had a molecular size of around 35 kDa and the AmCel-5B had a molecular size of around 37 kDa (FIG. 6). The recombinant AmCel-45A and AmCel-5B had the best carboxylmethyl cellulose (CMC) hydrolysis activity at pH 4.0 and 50° C. detected by a DNS method (FIGS. 7A-7B). The AmCel-45A and AmCel-5B had high thermostability after 12-hour incubation under different high temperatures (26° C.-70° C.) (FIGS. 7A-7B). In addition, the AmCel-45A had a broader pH tolerance after 12-hour incubation under pH 2-pH 10) (FIGS. 7A-7B). Interestingly, the endo-β-glucanase activities of AmCel-45A and AmCel-5B could be enhanced in the presence of various ions, including the bivalent metal ions $Ca^{++}$, $Cu^{++}$, $Mg^{++}$, $Mn^{++}$ and $Zn^{++}$ (FIGS. 9A and 10A). The addition of antioxidants, which include DTT and 2-Mercaptoethanol (2-ME), further enhanced the activity of these enzymes (FIGS. 9B and 10B). Other antioxidants including β-carotene, lutein, lycopene, astaxanthin, vitamin C, vitamin E, bioflavonoids, anthocyains, catechins, glutathione, inositol may also be functional. Furthermore, it was found that the combination of above ions and antioxidants was able to further enhance the activities of these enzymes. Table 2 shows that 2 mM $Co^{2+}$ and 10 mM dithiothreitol (DTT, a shylhydryl-containing antioxidant) plus 2 mM $Mn^{2+}$, respectively, could enhance the functions of the enzymes. To mimic the insect cellulase mixture in the digestive tract, a synergistic addition of AmCel-45A and AmCel-5B was found to exhibit a high activity in hydrolyzing pre-treated rice straw, and also could stimulate the activity of commercial enzymes (e.g., CELLUCLAST® 1.5 L, Novozyme) in catalyzing the hydrolysis of pre-treated rice straw (FIG. 8). Table 1 shows comparisons of enzyme activities for AmCel-45A, AmCel-5B and CELLUCLAST® 1.5 L in different substrates (AmCel-45A and AmCel-5B were performed at pH 4.0 and 50° C.; CELLUCLAST® 1.5 L was performed at pH 5.0 and 50° C. using 1% substrates).

TABLE 1

| | Specific activity (U*/mg protein) | | |
|---|---|---|---|
| Substrates | AmCel-45A | AmCel-5B | CELLUCLAST® 1.5L |
| CMC | 319.22 ± 9.3 | 18.57 ± 0.54 | 12.76 ± 0.23 |
| β-glucan | 1.12 ± 0.04 | 0.34 ± 0.02 | 0.26 ± 0.04 |
| Avicel | 0.35 ± 0.02 | 0.69 ± 0.05 | 1.27 ± 0.05 |
| Xylan (Oat spelt) | 0.71 ± 0.04 | 0.77 ± 0.04 | 22.76 ± 0.89 |
| Xylan (Birchwood) | 2.07 ± 0.07 | 3.35 ± 0.11 | 20.53 ± 0.52 |
| Cut filter paper | 0.19 ± 0.02 | 0.53 ± 0.04 | 1.88 ± 0.05 |
| Pretreated rice straw fibers | 0.11 ± 0.01 | 0.39 ± 0.03 | 0.21 ± 0.02 |

*1 U = 1 µmole glucose equivalent amount per minute by DNS method.
Assays of AmCel-45A and AmCel-5B were performed in the presence of 50 mM citrate buffer (pH 4.0) at 50° C.

TABLE 2

| | Specific activity (U*/mg protein) | | |
|---|---|---|---|
| Substrates | AmCel-45A[a] | AmCel-5B[b] | CELLUCLAST® 1.5L[c] |
| CMC | 807.12 ± 20.21 | 102.31 ± 4.05 | 12.76 ± 0.23 |
| β-glucan | 3.37 ± 0.11 | 1.97 ± 0.06 | 0.26 ± 0.04 |

*1 U = 1 µmole glucose equivalent amount per minute by DNS method.
[a]Assays were under 50 mM citrate buffer (pH 4.0) with 2 mM $CoCl_2$ at 50° C.
[b]Assays were under 50 mM citrate buffer (pH 4.0) with 10 mM DTT; 2 mM $MnCl_2$ at 50° C.
[c]Assays were under 50 mM citrate buffer (pH 4.0) at 50° C.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A composition comprising:
   (c) a first cellulase, comprising an amino acid sequence having, at least 90% identity to SEQ ID NO: 2; and
   (d) a second cellulase, comprising the amino acid sequence having at least 90% identity to SEQ ID NO: 4.

2. The composition of claim 1, further comprising at least one type of metal ion selected from the group consisting of $Ca^{++}$, $Co^{++}$, $Cu^{++}$, $Mg^{++}$, $Mn^{++}$ and $Zn^{++}$.

3. The composition of claim 1, further comprising an additional cellulase.

4. A method of hydrolyzing cellulosic material comprising:
   exposing the cellulosic material to an effective amount of the composition of claim 1.

5. A method of hydrolyzing cellulosic material comprising:
   exposing the cellulosic material to an effective amount of the composition of claim 2.

6. A method of hydrolyzing cellulosic material comprising:
   exposing the cellulosic material to an effective amount of the composition of claim 3.

7. An isolated cellulase comprising an amino acid sequence having at least 90% identity to an amino acid sequence selected from the group consisting of SEQ ID NOs: 2 and 4.

8. The isolated cellulase of claim 7, wherein the amino acid sequence of the isolated cellulase is SEQ ID NO: 2.

9. The isolated cellulase of claim 7, wherein the amino acid sequence of the isolated cellulase is SEQ ID NO: 4.

10. The composition of claim 3, wherein the additional cellulase comprises a cellulase from *Trichoderma reesei* ATCC 26921.

11. A method of hydrolyzing cellulosic material comprising:
    exposing the cellulosic material to an effective amount of the composition of claim 10.

12. The method of claim 4, wherein the cellulosic material is at least one selected from the group consisting of carboxymethyl cellulose (CMC), β-glucan, Xylan-oat spelt, and Xylan-Birch wood.

13. The method of claim 5, wherein the cellulosic material is at least one selected from the group consisting of carboxymethyl cellulose (CMC); β-glucan, Xylan-oat spelt, and Xylan-Birchwood.

14. The method of claim 6, wherein the cellulosic material is at least one selected from the group consisting of carboxymethyl cellulose (CMC), β-glucan, Xylan-oat spelt, and Xylan-Birchwood.

15. The composition of claim 1, further comprising one or more antioxidant agents selected from the group consisting of dithiothreito, 2-Mercaptoethanol, β-carotene, lutein, lycopene, astaxanthin, vitamin C, vitamin E, bioflavonoids, anthocyains, catechins, glutathione, and inositol.

16. The composition of claim 2, further comprising one or more antioxidant agents selected from the group consisting of dithiothreito, 2-Mercaptoethanol, β-carotene, lutein, lycopene, astaxanthin, vitamin C, vitamin E, bioflavonoids, anthocyains, catechins, glutathione, and inositol.

17. A method of hydrolyzing cellulosic material comprising:
   exposing the cellulosic material to an effective amount of the composition of claim 15.

18. A method of hydrolyzing cellulosic material comprising:
   exposing the cellulosic material to an effective amount of the composition of claim 16.

19. A composition comprising:
   (a) a first cellulase, comprising the amino acid sequence of SEQ ID NO: 2; or
   (b) a second cellulase, comprising the amino acid sequence of SEQ ID NO: 4; and
   (c) a third cellulase.

20. The composition of claim 19, wherein the third cellulase comprises a cellulase from *Trichoderma reesei* ATCC 26921.

* * * * *

SEQUENCE LISTING

<160> NUMBER OF SEQ ID NOS: 4

<210> SEQ ID NO 1
<211> LENGTH: 717
<212> TYPE: DNA
<213> ORGANISM: Anoplophora malasiaca

<400> SEQUENCE: 1

```
atgaagctgt tgttactaat tgctgctgtg ttttacacat tccatggatc gttctccaaa      60
gactacaatg tcgtgccaat agtgggcggc ataagtggaa ccggagtcac aacccgttac     120
tgggactgtt gtaaaccgtc atgtggttgg gctgaaaatt tgaaagtcga aactgacacc     180
cctgtagcga cttgttcagc tgacggatca actgtagtaa acgccagcgt ccaatcagct     240
tgtataggag gcgatgctta catgtgcagt aatcaacaac ccaaagcggt caatgaaacg     300
tttgctcttg gatttgtggc tgcttccttc accggaggtg ccgataccaa ctattgttgt     360
gcttgtgtgc gacttacctt ccagtctcct attcaaggca aacagatggt tgtacaagta     420
accaatactg gtggtgattt gggttccaat cattttgaca tcgcccttcc cggtggtggt     480
gtgggaatat tcactgaagg ttgttcttcg caatggggat gtcctagcaa tggctgggg t     540
gaccagtatg gcggtgttgc atcggaaagt gactgttcta cacttccagc agtcctccaa     600
gatggatgta aattccgttt tcagttcctg caaggcgcgt ctaaccctgg tgttaccttt     660
gaacaagtcg agtgtccatc cgagttgaca tctattactg gctgtaacta ttcctaa       717
```

<210> SEQ ID NO 2
<211> LENGTH: 238
<212> TYPE: PRT
<213> ORGANISM: Anoplophora malasiaca

<400> SEQUENCE: 2

```
Met Lys Leu Leu Leu Ile Ala Ala Val Phe Tyr Thr Phe His Gly
1               5                   10                  15

Ser Phe Ser Lys Asp Tyr Asn Val Val Pro Ile Val Gly Gly Ile Ser
            20                  25                  30

Gly Thr Gly Val Thr Thr Arg Tyr Trp Asp Cys Cys Lys Pro Ser Cys
        35                  40                  45

Gly Trp Ala Glu Asn Leu Lys Val Glu Thr Asp Pro Val Ala Thr
    50                  55                  60

Cys Ser Ala Asp Gly Ser Thr Val Val Asn Ala Ser Val Gln Ser Ala
65                  70                  75                  80

Cys Ile Gly Gly Asp Ala Tyr Met Cys Ser Asn Gln Gln Pro Lys Ala
                85                  90                  95

Val Asn Glu Thr Phe Ala Leu Gly Phe Val Ala Ala Ser Phe Thr Gly
            100                 105                 110

Gly Ala Asp Thr Asn Tyr Cys Cys Ala Cys Val Arg Leu Thr Phe Gln
        115                 120                 125

Ser Pro Ile Gln Gly Lys Gln Met Val Val Gln Val Thr Asn Thr Gly
    130                 135                 140

Gly Asp Leu Gly Ser Asn His Phe Asp Ile Ala Leu Pro Gly Gly Gly
145                 150                 155                 160

Val Gly Ile Phe Thr Glu Gly Cys Ser Ser Gln Trp Gly Cys Pro Ser
                165                 170                 175

Asn Gly Trp Gly Asp Gln Tyr Gly Gly Val Ala Ser Glu Ser Asp Cys
            180                 185                 190
```

```
Ser Thr Leu Pro Ala Val Leu Gln Asp Gly Cys Lys Phe Arg Phe Gln
    195                 200                 205

Phe Leu Gln Gly Ala Ser Asn Pro Gly Val Thr Phe Glu Gln Val Glu
    210                 215                 220

Cys Pro Ser Glu Leu Thr Ser Ile Thr Gly Cys Asn Tyr Ser
225                 230                 235

<210> SEQ ID NO 3
<211> LENGTH: 978
<212> TYPE: DNA
<213> ORGANISM: Anoplophora malasiaca

<400> SEQUENCE: 3
atgaacaagt caattttgtc gatttgtctg gtcgtgctgg ccttgtatat cgattcctcg      60
atatctaagg atgccggcca agaaacagtt tccaagcacg gtaaactgtc cgtgaagggt     120
gccaacatag tgaaccagaa tggcgagata gtccagttga aaggcatgtg tttgtactgg     180
agcatatgga agccacagta ctggaacgaa gaaacagtcc aaggaattca cgactcgtgt     240
cactccaacg ttatccgagc ttccatgggc gtcgagacaa cgatggcgg ttacttaact      300 gacccagacg gtcagatgaa gctagtggaa ccgtcatcg aggcagcaat taaacatgac      360
ctctacatca tcgtggactg gcacgaagaa aaggcaggca ctcaccaaac acaagctgta     420
gacttctttg acaaaatctc taagaaatat ggaagctacc caaatctcat gtacgaaacc     480
ttcaacgaac caactaccca gtcctggtcc agcgtgctta accgtatca tgaagccgtt      540 atcaaagcca tccgtgccaa tgacccagac aacatcatca tttgcggtac tggccaatgg    600
tcacagagag tcgacgaagc cgccgatgat cctatcacga gctacagcaa tatcatgtac    660
actttgcact tctacgctgg cacccataag caatggctcc gtgacctcac tcaaggcgct    720
atcgacaaag gtcttcccat cttcgttaca gaatatggca ctgataatgt agatgtggtc    780
aattgggtgg atcccgaaga tcccagctt tggtgggact tctgtgataa aaataacttg     840
tcctatacta actgggccat atgcgacgtg gccgaggcat ctgctgcttt gatagcagac    900
acccccccca ataaagtatg ccaacaagat tacctgacgg aatccggctt gctcgttgta    960
gcccagaata agaaatga                                                  978

<210> SEQ ID NO 4
<211> LENGTH: 324
<212> TYPE: PRT
<213> ORGANISM: Anoplophora malasiaca

<400> SEQUENCE: 4

Met Asn Lys Ser Ile Leu Ser Ile Cys Leu Val Val Leu Ala Leu Tyr
1               5                   10                  15

Ile Asp Ser Ser Ile Ser Lys Asp Ala Gly Gln Glu Thr Val Ser Lys
            20                  25                  30

His Gly Lys Leu Ser Val Lys Gly Ala Asn Ile Val Asn Gln Asn Gly
        35                  40                  45

Glu Ile Val Gln Leu Lys Gly Met Cys Leu Tyr Trp Ser Ile Trp Lys
    50                  55                  60

Pro Gln Tyr Trp Asn Glu Glu Thr Val Gln Gly Ile His Asp Ser Cys
65                  70                  75                  80

His Ser Asn Val Ile Arg Ala Ser Met Gly Val Glu Thr Asn Asp Gly
                85                  90                  95

Gly Tyr Leu Thr Asp Pro Asp Gly Gln Met Lys Leu Val Glu Thr Val
            100                 105                 110
```

-continued

```
Ile Glu Ala Ala Ile Lys His Asp Leu Tyr Ile Ile Val Asp Trp His
        115                 120                 125

Glu Glu Lys Ala Gly Thr His Gln Thr Gln Ala Val Asp Phe Phe Asp
    130                 135                 140

Lys Ile Ser Lys Lys Tyr Gly Ser Tyr Pro Asn Leu Met Tyr Glu Thr
145                 150                 155                 160

Phe Asn Glu Pro Thr Thr Gln Ser Trp Ser Ser Val Leu Lys Pro Tyr
                165                 170                 175

His Glu Ala Val Ile Lys Ala Ile Arg Ala Asn Asp Pro Asp Asn Ile
                180                 185                 190

Ile Ile Cys Gly Thr Gly Gln Trp Ser Gln Arg Val Asp Glu Ala Ala
        195                 200                 205

Asp Asp Pro Ile Thr Ser Tyr Ser Asn Ile Met Tyr Thr Leu His Phe
    210                 215                 220

Tyr Ala Gly Thr His Lys Gln Trp Leu Arg Asp Leu Thr Gln Gly Ala
225                 230                 235                 240

Ile Asp Lys Gly Leu Pro Ile Phe Val Thr Glu Tyr Gly Thr Asp Asn
                245                 250                 255

Val Asp Val Val Asn Trp Val Asp Pro Glu Glu Ser Gln Leu Trp Trp
            260                 265                 270

Asp Phe Cys Asp Lys Asn Asn Leu Ser Tyr Thr Asn Trp Ala Ile Cys
        275                 280                 285

Asp Val Ala Glu Ala Ser Ala Ala Leu Ile Ala Asp Thr Pro Pro Asn
    290                 295                 300

Lys Val Cys Gln Gln Asp Tyr Leu Thr Glu Ser Gly Leu Leu Val Val
305                 310                 315                 320

Ala Gln Asn Lys
```